United States Patent
Ivancev et al.

(10) Patent No.: US 8,636,789 B2
(45) Date of Patent: Jan. 28, 2014

(54) PARAPLEGIA PREVENTION VALVE FOR STENT GRAFTS

(75) Inventors: Krasnodar Ivancev, London (GB); Piotr Miroslaw Kasprzak, Regensburg (DE); David Ernest Hartley, Wannanup (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/467,330

(22) Filed: May 9, 2012

(65) Prior Publication Data
US 2012/0290069 A1    Nov. 15, 2012

(30) Foreign Application Priority Data
May 9, 2011    (AU) ................................ 2011202120

(51) Int. Cl.
*A61F 2/06*    (2013.01)

(52) U.S. Cl.
USPC ........................................ 623/1.13; 623/1.25

(58) Field of Classification Search
USPC .......... 623/1.11, 1.13, 1.15, 1.24–1.27, 1.35, 623/1.37, 1.44, 2.3, 1.43
See application file for complete search history.

(56) References Cited

U.S. PATENT DOCUMENTS

| | | | |
|---|---|---|---|
| 2003/0204243 A1 | 10/2003 | Shiu | |
| 2005/0059923 A1* | 3/2005 | Gamboa | ........................... 604/9 |
| 2007/0219621 A1 | 9/2007 | Hartley et al. | |
| 2007/0288086 A1* | 12/2007 | Kalmann et al. | ............. 623/1.24 |
| 2008/0312732 A1* | 12/2008 | Hartley et al. | ............... 623/1.13 |

FOREIGN PATENT DOCUMENTS

| | | |
|---|---|---|
| WO | 2007124053 A1 | 11/2007 |
| WO | 2008057568 A1 | 5/2008 |
| WO | 2008057569 A1 | 5/2008 |
| WO | 2011047004 A1 | 4/2011 |

* cited by examiner

*Primary Examiner* — Thomas J Sweet
*Assistant Examiner* — Christopher D Prone
(74) *Attorney, Agent, or Firm* — Richard J. Godlewski (57)    ABSTRACT

A stent graft defining a main lumen bounded by a wall of graft material is disclosed. The stent graft has a valve portion between proximal and distal portions. The valve portion is formed by a wall portion having a part-circumferential double layer portion comprising an inner underlap portion and an outer overlap portion, the double layer portion forming a passageway parallel to the main lumen. The passageway has an entrance mouth and an exit mouth. The passageway has an open condition where the underlap and overlap portions are spaced apart to form a vent lumen. The wall portion is broken by a narrow cut. The cut is openable by relative radial movement between its edges. This allows re-perfusion of an aneurism and perfusion of blood from within the lumen out towards blood vessels such as intercostals and can assist in minimizing the chance of paraplegia.

11 Claims, 12 Drawing Sheets

PARAPLEGIA PREVENTION VALVE FOR STENT GRAFTS

FIELD OF INVENTION

This invention relates to a medical device and more particularly to an implantable endovascular device.

BACKGROUND OF THE INVENTION

This invention will be discussed in general with respect to aortic aneurysms and the use of an implantable device such as a stent graft to bridge an aneurysm and in particular in the descending aorta but the invention is not so limited and may be used for any region of the human or animal body and any type of implantable device.

A stent graft can be used to bridge an aortic aneurysm but where there are side branch arteries from the aorta it is necessary to have side branches extending from the stent graft to give a blood supply to as many side branch arteries as possible.

There are four main side branch arteries in the descending aorta. These are the celiac artery, the superior mesenteric artery, the right renal artery and the left renal artery. There are also a number of other minor side branch arteries but these are smaller and generally cannot be catheterised to enable placement of a side branch graft. One of these sets of arteries is the intercostal arteries. Stent grafts can block or inhibit spinal cord blood supply through these arteries, at least temporarily.

After an endovascular operation to place a stent graft into the descending aorta to repair a thoraco-abdominal aortic aneurysm (TAAA) for instance, the human or animal body can in time adapt to lack of blood supply from some arteries which are occluded by the stent graft. For instance blood supply via the intercostal arteries to the spinal cord can be alternatively achieved via other arteries such as for instance the celiac artery, the superior mesenteric artery, lumbar and internal iliac arteries.

There can be a problem, however, of blood supply immediately after an operation, causing a risk of paraplegia or spinal cord ischemia, and it is the object of this invention to provide a possible solution or at least provide the physician with a useful alternative.

DESCRIPTION OF THE INVENTION

According to a first aspect of the invention there is provided a stent graft defining a main lumen bounded by a wall of biocompatible graft material, the stent graft having a proximal end, a proximal portion, a distal end, a distal portion and a valve portion between the proximal and distal portions, the valve portion formed by a wall portion having a part-circumferential double layer portion comprising an inner underlap portion and an outer overlap portion, the double layer portion forming a passageway parallel to the main lumen, the passageway having an entrance mouth and an exit mouth, the exit mouth closer to the proximal end of the stent graft than the entrance mouth, the passageway having a closed condition where the underlap and overlap portions are in contact and an open condition where the underlap and overlap portions are spaced apart to form a vent lumen, the wall portion broken by a narrow cut or slot, the cut or slot having a first edge and a second edge, wherein the cut or slot is openable by relative radial movement of the first edge away from the second edge.

In one form, one of the underlap and overlap portions comprises a sheet of biocompatible graft material attached to the wall portion.

In one form, the exit mouth is substantially crescent shaped when in the open condition.

In one form the proximal end of the stent graft has a selected diameter and the valve portion has a reduced diameter, the reduced diameter less than the selected diameter.

In one form, the stent graft further comprises a plurality of external zig zag stents longitudinally spaced apart on an outside surface of the wall of biocompatible graft material and at least one internal stent within the valve portion between the proximal and distal ends, the internal stent having at least first, second and third struts, the second strut extending between the first and third struts.

In one form, the sheet comprises, a first edge, a second edge opposite the first edge, a distal edge and a proximal edge, the first edge sewn to the wall portion adjacent to the first strut of the at least one internal stent, the second edge sewn to the wall portion adjacent to the third strut of the at least one internal stent and the proximal edge sewn along a line between a pair of adjacent points of the internal stent, wherein the sheet is biased radially outwards by the second strut.

In one form, the valve comprises a support wire extending between the pair of adjacent points of the strut.

In one form, the support wire is an inverted U-shape when the proximal end is orientated above the distal end.

In one form, the stent graft further comprises a guide wire extending from beyond the distal end through the valve portion and through the vent lumen and out through the exit mouth, the guide wire provided for guiding a valve opening device.

According to a second aspect of the invention there is provided a stent graft defining a main lumen bounded by a wall of biocompatible graft material, the stent graft having a proximal end and a distal end and a valve portion between the proximal and distal ends, the valve portion formed by a wall portion having a part-circumferential double layer portion comprising an inner underlap portion and an outer overlap portion, the double layer portion forming a passageway parallel to the main lumen, the passageway having an entrance mouth and an exit mouth, the exit mouth closer to the proximal end of the stent graft than the entrance mouth, the passageway having a closed condition where the underlap and overlap portions are in contact and an open condition where the underlap and overlap portions are spaced apart to form a vent lumen, wherein the exit mouth is substantially crescent shaped when in the open condition.

In one form, the stent graft further comprises a guide wire extending from beyond the distal end through the valve portion and through the vent lumen and out through the exit mouth, the guide wire provided for guiding a valve opening device.

According to a third aspect of the invention there is provided a stent graft for deployment into the aorta of a patient, the stent graft comprising a tubular body of a biocompatible graft material, the tubular body having a wall defining a main lumen therethrough, the tubular body comprising a proximal portion of a selected diameter and a portion of reduced diameter less than the selected diameter distal of the proximal portion and a proximal tapered portion extending between the proximal portion and the portion of reduced diameter, a plurality of low profile side arms in the portion of reduced diameter or the tapered portion, each low profile side arm comprising a respective side arm lumen therethrough and the main lumen being in fluid communication with the respective side arm lumens, the side arms being each for connection of an arm extension to an aortic branch vessel, a paraplegia prevention valve in fluid communication with the main lumen and open to external of the tubular body in a region defined by the portion of reduced diameter and the tapered portion, the valve formed by a portion of the wall having a part-circumferential double layer portion comprising an inner underlap portion and an outer overlap portion, the double layer portion forming a passageway parallel to the main lumen, the passageway having an entrance mouth and an exit mouth, the exit mouth closer to the proximal end of the stent graft than the entrance mouth, the passageway having a closed condition where the underlap and overlap portions are in contact and an open condition where the underlap and overlap portions are spaced apart to form a vent lumen, the wall portion broken by a narrow cut or slot, the cut or slot having a first edge and a second edge, wherein the cut or slot is openable by relative radial movement of the first edge away from the second edge.

In one form, the plurality low profile side arms in the portion of reduced diameter or the tapered portions comprise four low profile side arms, one each for a celiac artery, a superior mesenteric artery, a right renal artery and a left renal artery of a patient.

In one form, the exit mouth is substantially crescent shaped when in the open condition.

In one form, the stent graft further comprises a plurality of external zig zag stents longitudinally spaced apart on an outside surface of the wall of biocompatible graft material and at least one internal stent within the valve portion between the proximal and distal ends, the internal stent having at least first, second and third struts, the second strut extending between the first and third struts.

In one form, the sheet comprises, a first edge, a second edge opposite the first edge, a distal edge and a proximal edge, the first edge sewn to the wall portion adjacent to the first strut of the at least one internal stent, the second edge sewn to the wall portion adjacent to the third strut of the at least one internal stent and the proximal edge sewn along a line between a pair of adjacent points of the strut, wherein the sheet is biased radially outwards by the second strut.

In one form, the valve comprises a support wire extending between the pair of adjacent points of the strut.

In one form, the support wire is an inverted U-shape when the proximal end is orientated above the distal end.

Hence it will be seen that by the various forms of the invention there is provided an arrangement by which, at the time of placement of the implantable device such as a stent graft and side branches, there is a means of supplying blood to the intercostal arteries for instance.

Immediately after an operation to deploy an endovascular stent graft, there may be insufficient blood to the intercostal arteries for instance. The continued perfusion blood to an annular space outside the stent graft in the region of the intercostal arteries enables a continued supply of blood to the vertebral region which can prevent paraplegia.

BRIEF DESCRIPTION OF THE DRAWINGS

This then generally describes the invention but to assist with understanding reference will now be made to the accompanying drawings In the drawings.

DESCRIPTION OF PREFERRED EMBODIMENTS

Figure 1:
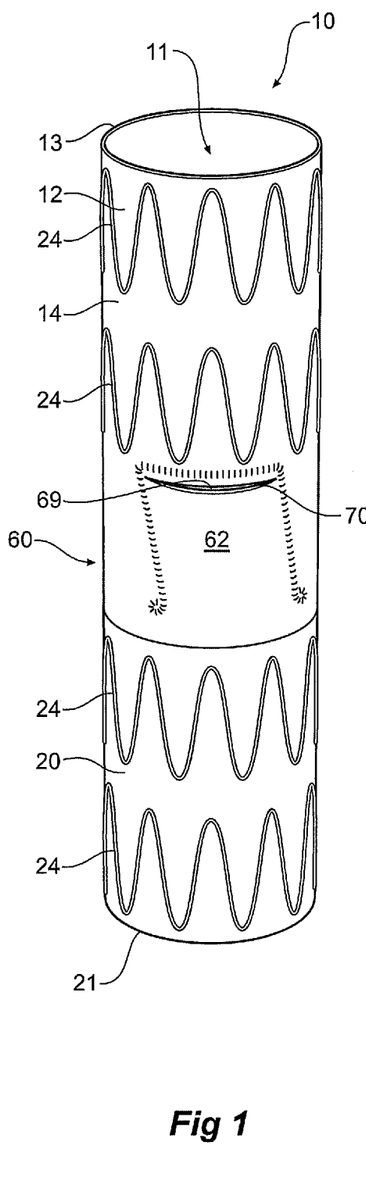
FIG. 1 shows a perspective view of a stent graft according to a first embodiment of the invention.
Figure 4A:
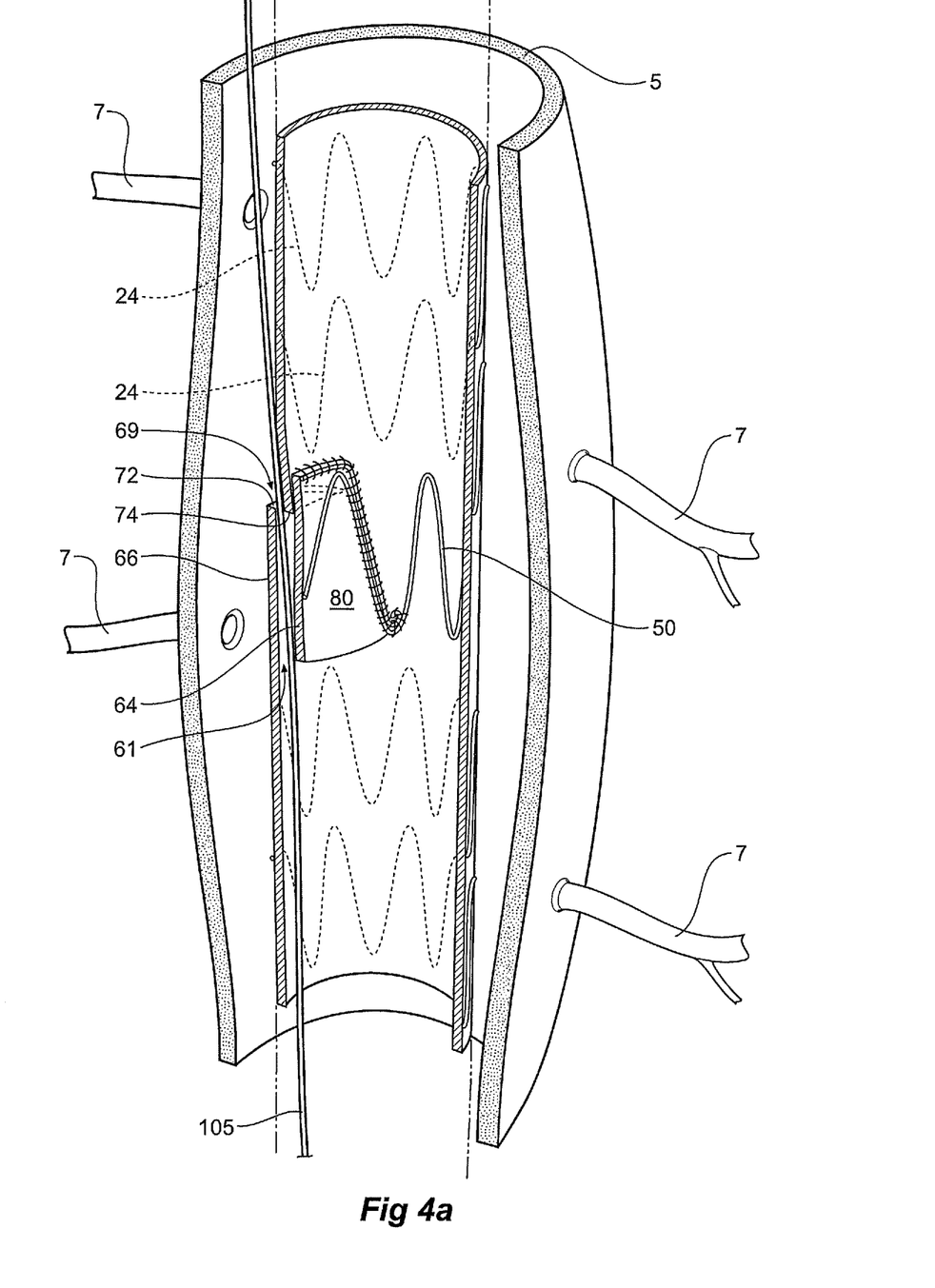
FIG. 4a shows a perspective cut-away view of the stent graft of FIG. 2.
Figure 4B:
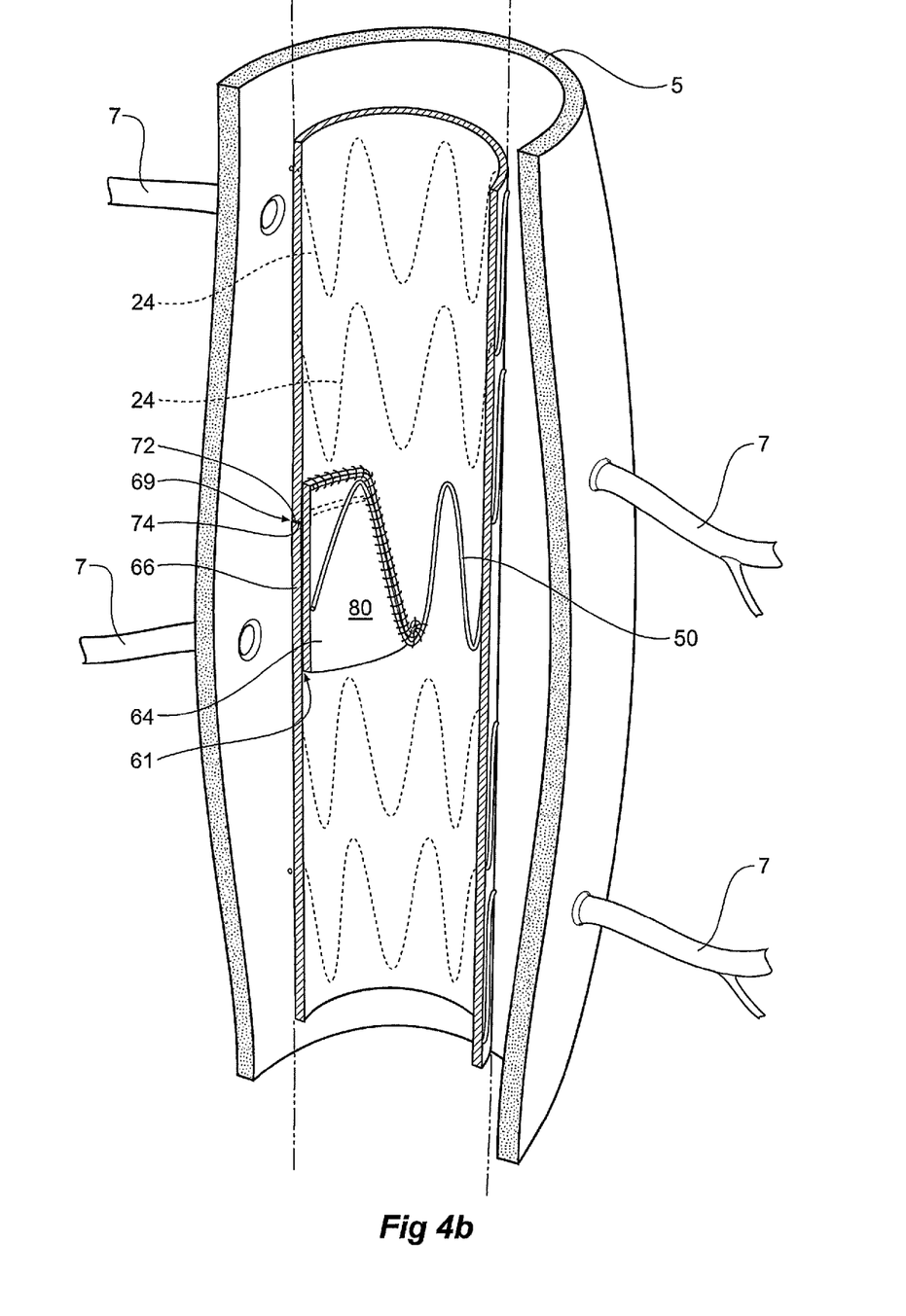
FIG. 4b is the same view as that of FIG. 4a, but with a wire removed.

Referring to FIG. 1, a stent graft 10 according to a first embodiment of the invention is shown. The stent graft 10 will find many uses and will commonly form a part of a more complex stent graft such as the stent graft 100 shown in FIG. 13. FIGS. 4a and 4b show a perspective cut-away view of the stent graft 10 in situ within a descending aorta 5 having intercostals 7.

The stent graft 10 has an exit mouth 69 that is not intended to be connected to a side branch artery of the aorta but is used to provide temporary perfusion to external of the stent graft 10 after deployment of the stent graft 10 into the aorta 5.

The stent graft 10 shown in FIG. 1 comprises a tubular body 12 of a biocompatible graft material. The stent graft 10 defines a main lumen 11 and has a proximal portion 14 adjacent a proximal end 13 and a distal portion 20 adjacent a distal end 21. A valve portion 60 is formed between the proximal and distal portions 14, 20. The valve portion 60 is formed by a wall portion 62 having a part-circumferential double layer portion comprising an inner underlap portion 64 and an outer overlap portion 66 as can bee seen in FIG. 4a. The double layer portion forms a passageway parallel to the main lumen, the passageway having an entrance mouth 61 and an exit mouth 69 as is most clearly shown in FIGS. 4a and 5. The exit mouth 69 is closer to the proximal end 14 of the stent graft than the entrance mouth 61.

Figure 2:
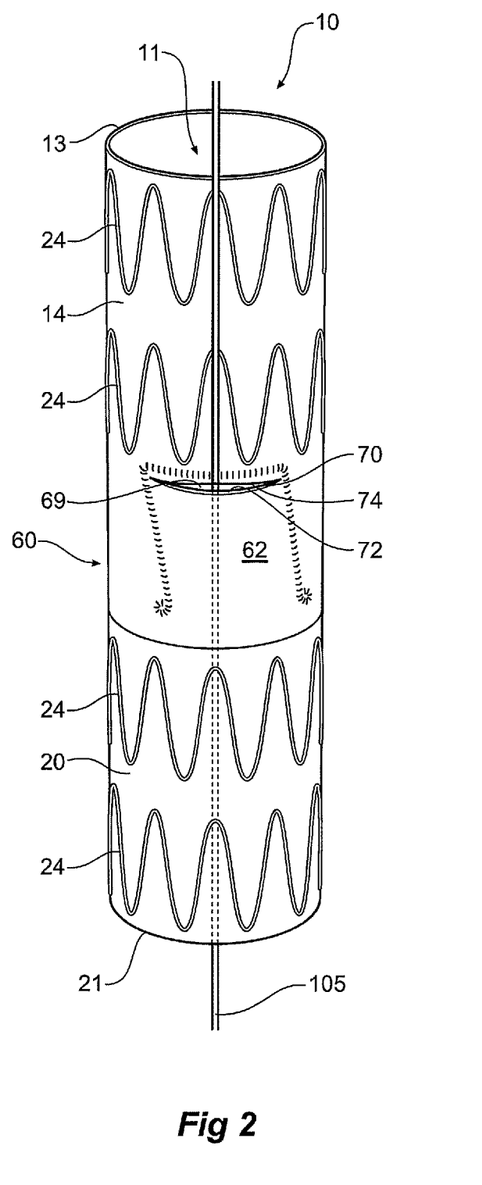
FIG. 2 is a similar view to that of FIG. 1 but shows the stent graft pre-loaded with a wire.
Figure 5:
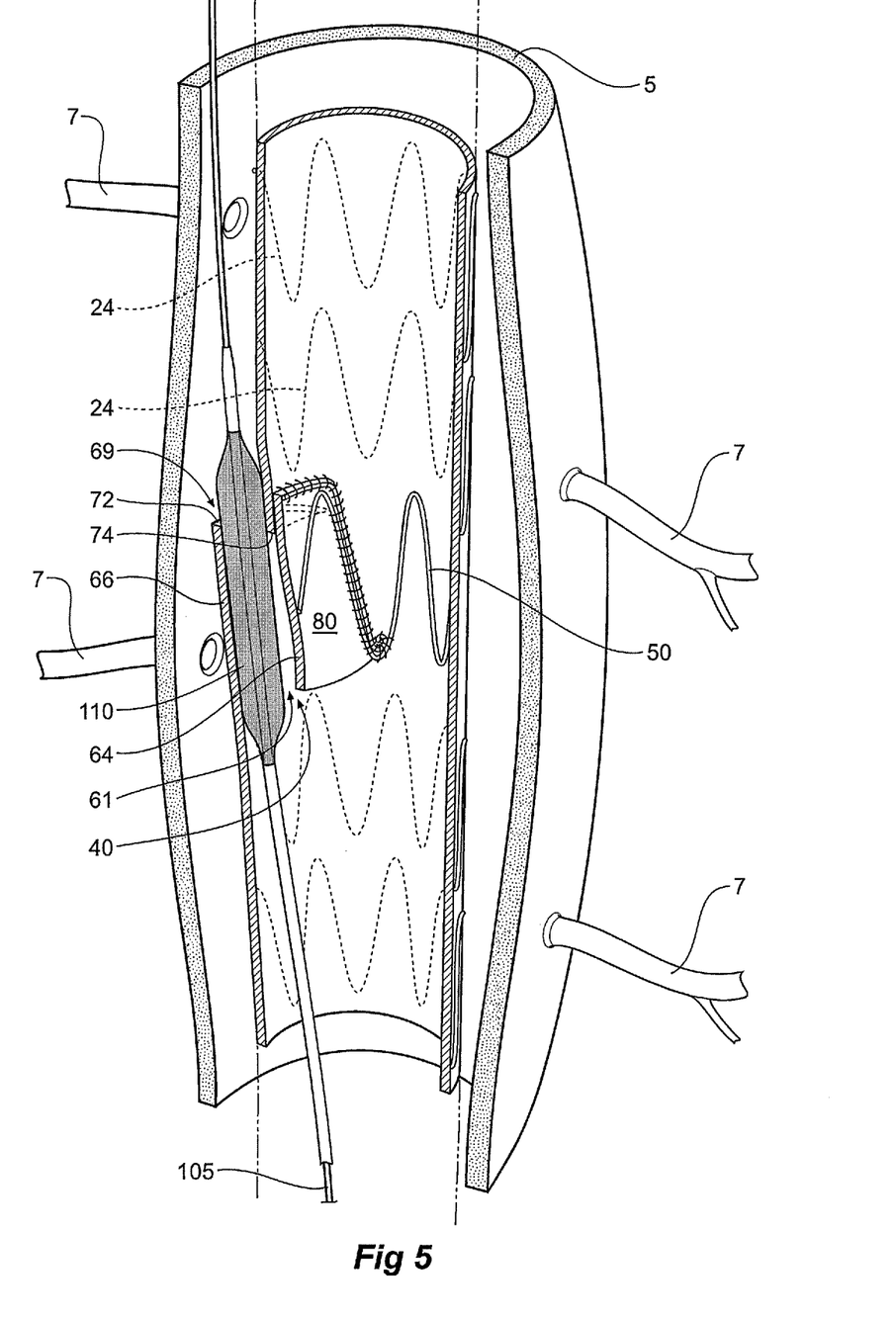
FIG. 5 is a similar view to that of FIG. 4a but shows a valve of stent graft in an open condition.
Figure 6:
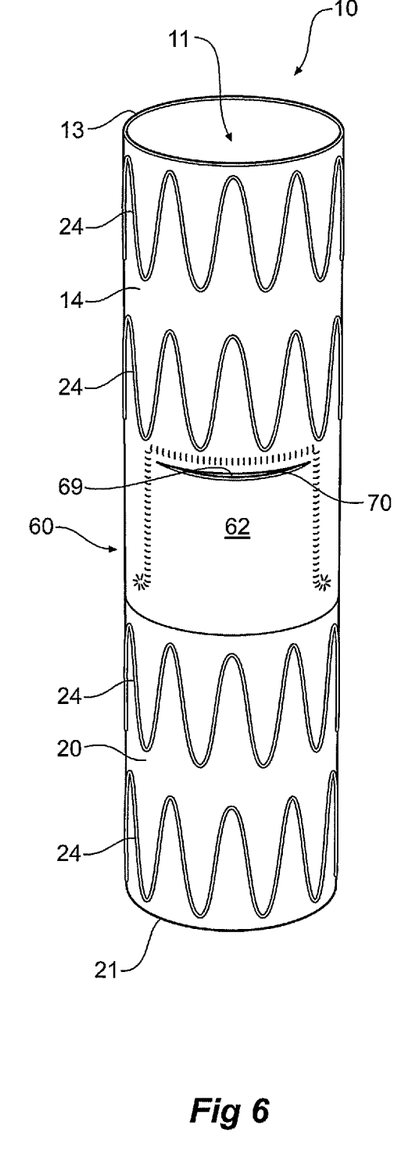
FIG. 6 shows a perspective view of a stent graft according to a second embodiment of the invention.
Figure 7:
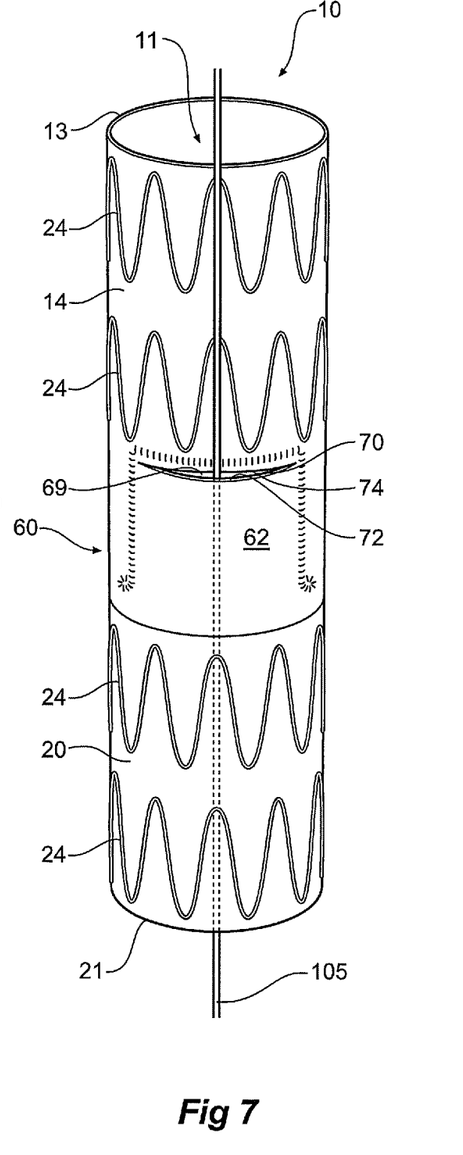
FIG. 7 is a similar view to that of FIG. 6 but shows the stent graft pre-loaded with a wire.
Figure 8:
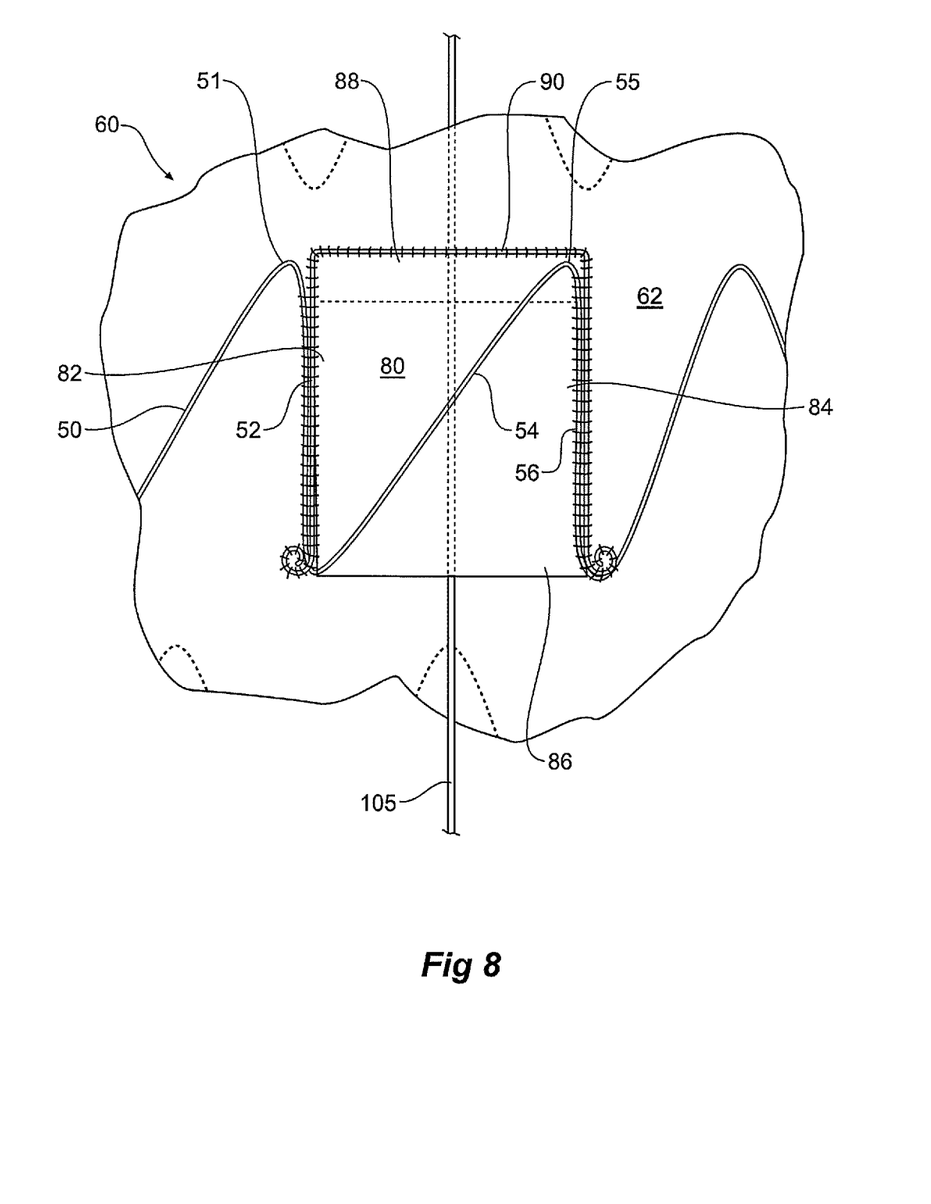
FIG. 8 shows a detailed view of a portion of the inside of the stent graft shown in FIG. 7.
Figure 9:
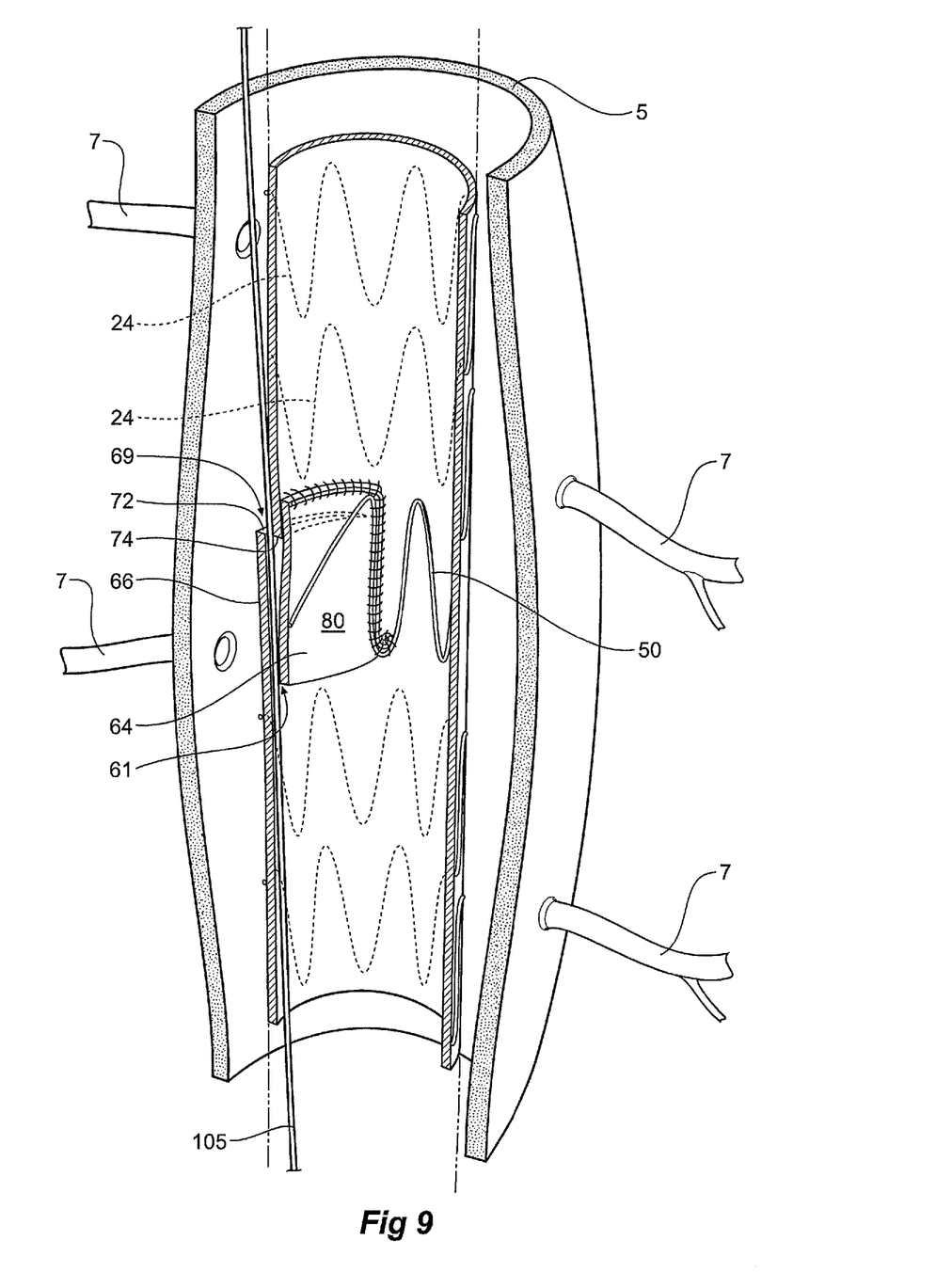
FIG. 9 shows a perspective cut-away view of the stent graft of FIG. 7.

The passageway has a closed condition where the underlap and overlap portions 64, 66 are in contact, as is shown in FIG. 4b, and an open condition where the underlap and overlap portions 64, 66 are spaced apart to form a vent lumen 40 as is shown in FIG. 5. The wall portion is broken by a narrow cut or slot 70 as can been seen in FIGS. 1 and 2. The cut or slot 70 has a first edge 72 and a second edge 74, and the cut or slot is openable by relative radial movement of the first edge 72 away from the second edge 74. Returning to FIG. 2, it can be seen that the exit mouth 69 is substantially crescent shaped when in the open condition.

Figure 3:
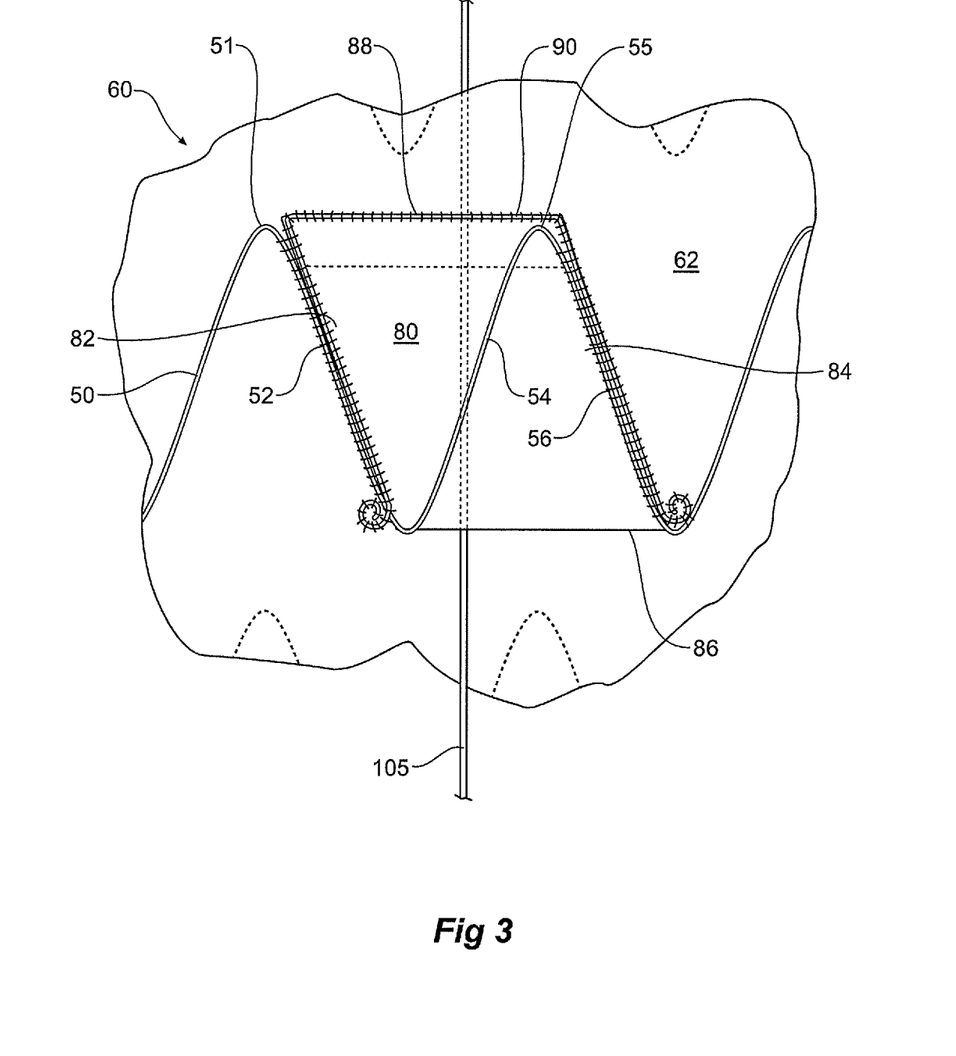
FIG. 3 shows a detailed view of a portion of the inside of the stent graft shown in FIG. 2.

Turning now to FIGS. 3 and 4, a valve portion 60 can be seen from within the stent graft 10 in a cutaway view. The underlap and overlap portions 64, 66 comprise a sheet 80 of biocompatible graft material attached to the wall portion 62. FIG. 4a shows a plurality of external zig zag stents 24 longitudinally spaced apart on an outside surface of the wall of biocompatible graft material. An internal stent 50 within the valve portion 60 is also provided. The internal stent 50 has first, second and third struts 52, 54, 56 with the second strut 54 extending between the first and third struts 52, 56. With the embodiment illustrated, the internal stent is a nitinol (metal alloy of nickel and titanium) stent. In other embodiments of the invention, stainless steel stents may be used in which case the struts 52, 54 and 56 would be substantially more parallel and more closely spaced within the graft than the nitinol stents struts shown in FIGS. 3 and 4a.

Referring again to FIG. 3, the construction at the valve portion 60 is shown. The sheet 80 is in the shape of a parallelogram and comprises a first edge 82, a second edge 84 opposite the first edge 82, a distal edge 86 and a proximal edge 88. The first edge 82 is sewn to the wall adjacent to the first strut 52 of the internal stent 50, a second edge 84 is sewn to the wall adjacent to the third strut 56 of the internal stent 50 and the proximal edge 88 is sewn along a line between a pair of adjacent points 51, 55 of the internal stent 50.

The sheet 80 is biased radially outwards by the second strut 54. This biases the valve into the closed condition as is shown in FIG. 4b.

A support wire 90 extending between the pair of adjacent points of the strut 51, 55 is shown in FIG. 3. The support wire is an inverted U-shape when the stent graft 10 is viewed with its proximal end orientated above its distal end. Curled ends are provided to avoid puncture points.

Referring now to FIGS. 6 to 9, a stent graft according to a second embodiment of the invention is shown. This embodiment is similar to the first embodiment except that the sheet 80 at the valve portion 60 is in the shape of a rectangle and the internal stent 50 is shaped differently with struts 52 and 54 orientated along a longitudinal axis of the stent graft 10.

Figure 10:
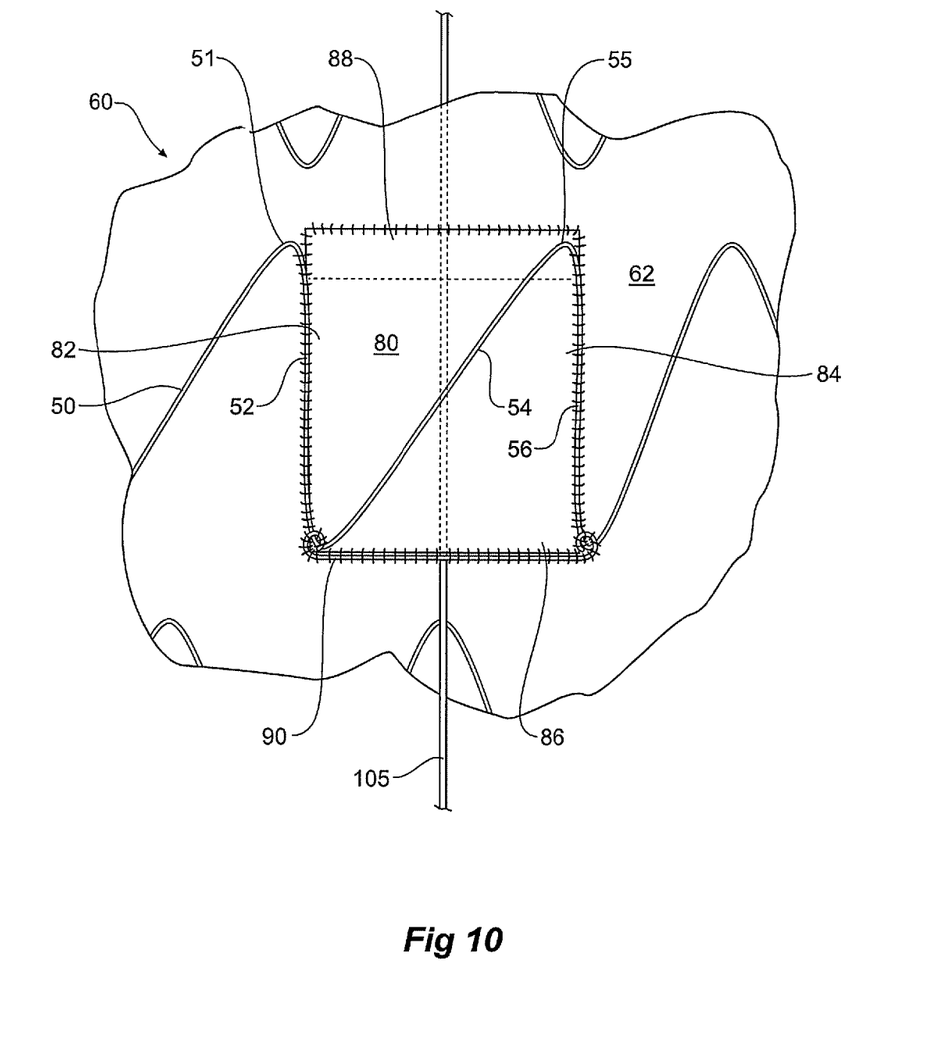
FIG. 10 shows a detailed view of a portion of the inside of the stent graft shown in FIG. 7, the stent graft according to a third embodiment which has an alternative valve arrangement.

Referring now to FIG. 10, a stent graft according to a third embodiment of the invention is shown. This embodiment is similar to the second embodiment except that the support wire 90 is positioned adjacent to the entrance mouth 61. This may facilitate gaining access though the valve where the stent graft 10 has not been pre-loaded with a wire 105 or where the wire 105 has been extracted and it is desired to re-insert the wire 105. Other arrangements at the entrance mouth may be provide to facilitate such access.

Figure 11:
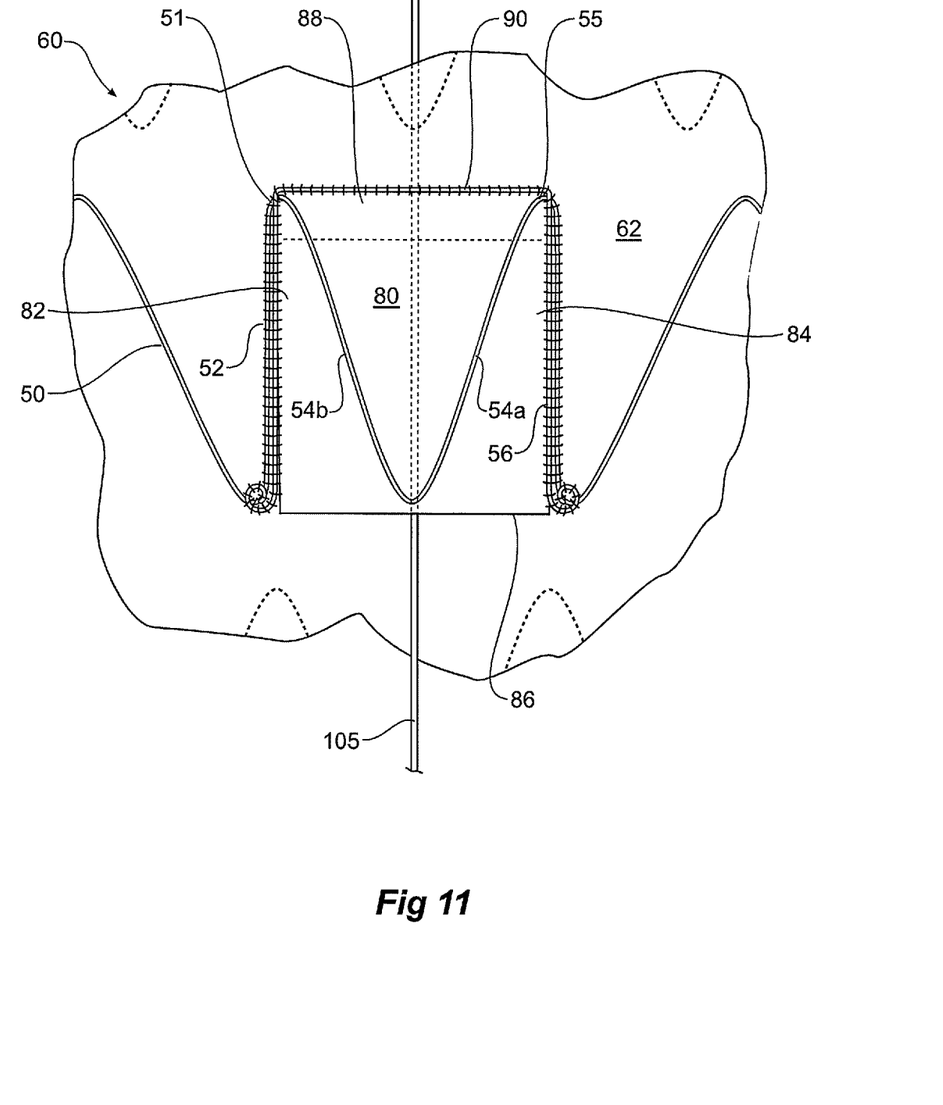
FIG. 11 shows a detailed view of a portion of the inside of the stent graft similar to that shown in FIG. 7, the stent graft according to a fourth embodiment which has a yet further alternative valve arrangement.

Referring now to FIG. 11, a stent graft according to a fourth embodiment of the invention is shown. This embodiment is similar to the second embodiment except that the internal stent 50 is "M" shaped having an two struts 54a and 54b biasing the sheet 80 radially outwards so as to bias the valve into the closed condition as is shown in FIG. 4b.

Figure 12:
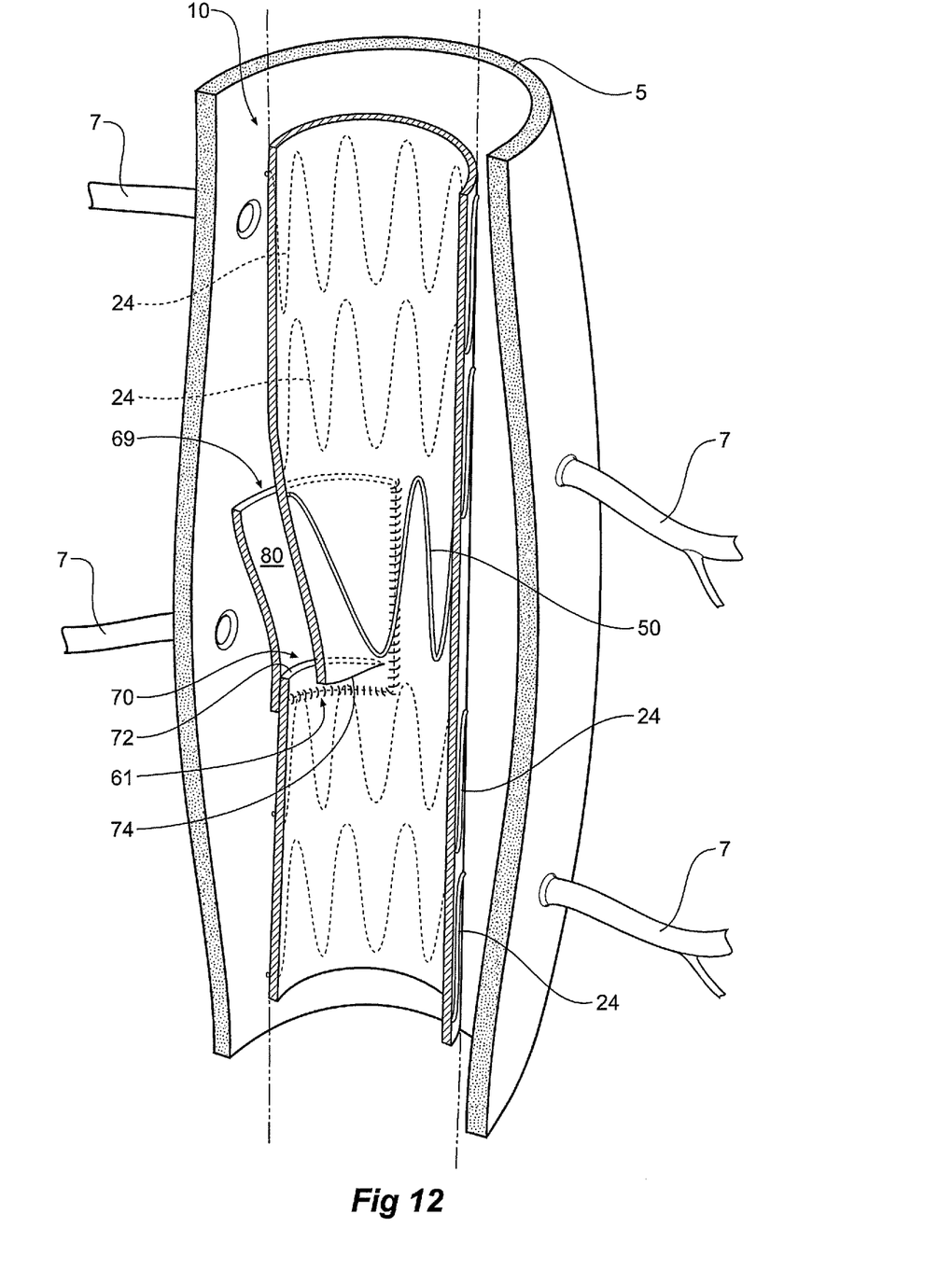
FIG. 12 shows a perspective cut-away view of a stent graft according to a fifth embodiment of the invention.

Referring now to FIG. 12, a stent graft according to a fifth embodiment of the invention is shown. With this embodiment of the invention, the sheet 80 is located outside of the lumen 11 rather than inside the lumen 11. With this arrangement, the narrow cut or slot 70 forms the entrance mouth 61 rather than the exit mouth 69. With this embodiment, when the valve is closed, a smooth internal wall to the lumen 11 is provided.

Figure 13:
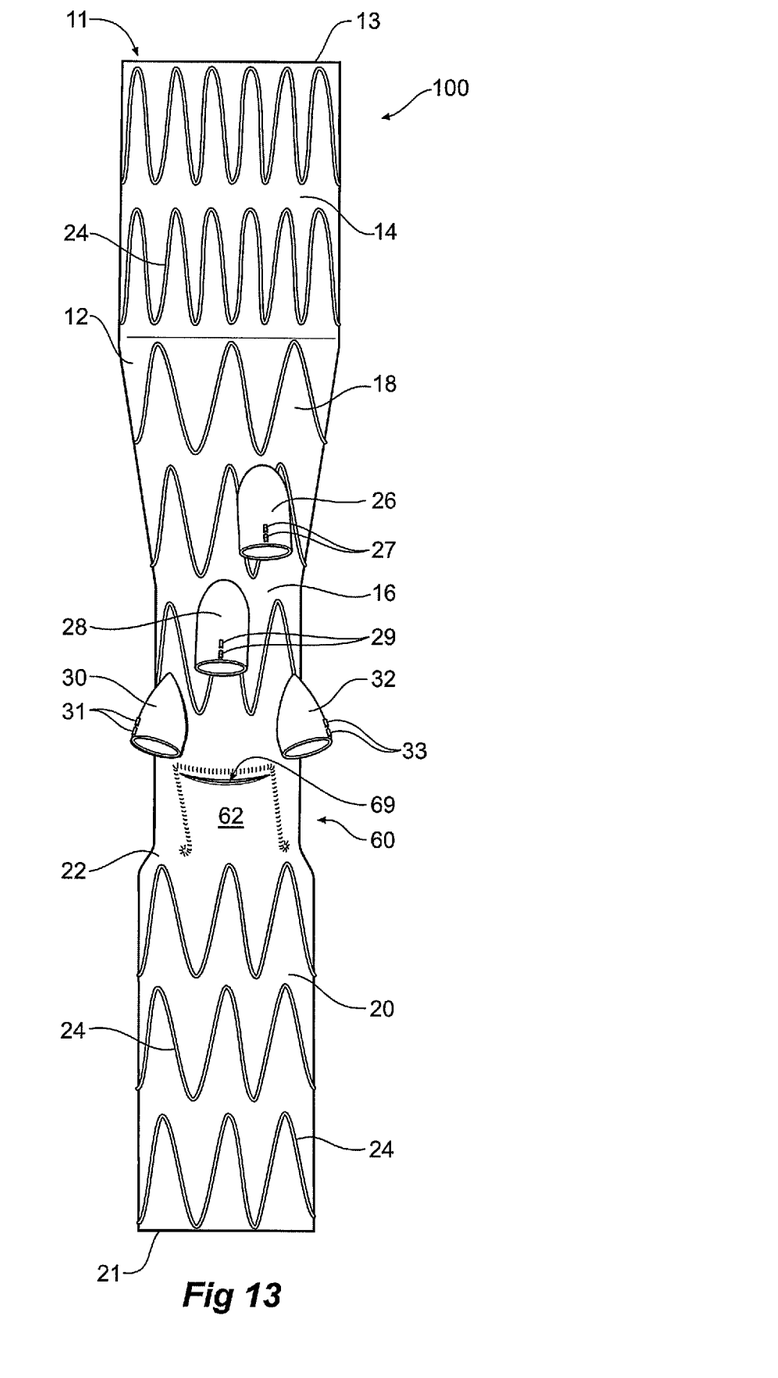
FIG. 13 shows a perspective view of a stent graft according to a sixth embodiment of the invention.

Referring now to FIG. 13, a stent graft according to a sixth embodiment of the invention is shown. Again a tubular body 12 of a biocompatible graft material is provided. The tubular body 12 has a main lumen 11 through it. The tubular body 12 comprises a proximal portion 14 of a selected diameter, a distal portion 20 and a portion of reduced diameter 16 between the proximal and distal portions 14, 20 having a diameter less than the selected diameter. A proximal tapered portion 18 extends between the proximal portion 14 and the portion of reduced diameter 16.

The distal portion 20 has a diameter less than the selected diameter and greater than that of the portion of reduced diameter 16 distal of the proximal portion. A distal tapered portion 22 extends between the distal portion 20 and the portion of reduced diameter 16. In this embodiment the proximal portion has a diameter of approximately 34 mm, the distal portion has a diameter of approximately 24 mm and the portion of reduced diameter has a diameter of approximately 20 mm.

Each of the proximal portion, the distal portion and the portion of reduced diameter are supported by stents 24 affixed to the graft material by stitching, adhesive or other method of affixation. The stents may be inside or outside of the tubular body. Each of the stents is preferably a self expanding Gianturco Z-stent formed from Nitinol or stainless steel wire.

There are four low profile side arms 26, 28, 30 and 32 extending from fenestrations in the portion of reduced diameter 16 or the proximal tapered portion 18. Each low profile side arm comprises a respective side arm lumen therethrough and the main lumen is in fluid communication with the respective side arm lumens. Each of the four low profile side arms 26, 28, 30 and 32 are supported by stent structures and can have reinforcing rings at their internal and external ends.

The four low profile side arms 26, 28, 30 and 32 are intended in use to receive extension side arms for entry into the celiac artery, the superior mesenteric artery, the right renal artery and the left renal artery respectively.

US Patent Application Publication Number 20070219621 entitled "Side Branch Stent Graft Construction" discloses various forms of low profile side arms and the teachings there are incorporated herein in their entirety.

The tubular body 12 also includes a paraplegia prevention valve in fluid communication with the main lumen 11 and open to external of the tubular body in a region defined by the portion of reduced diameter 16 and the proximal tapered portion 14. The valve is formed by a portion of the wall having a part-circumferential double layer portion comprising an inner underlap portion 64 and an outer overlap portion 66.

The double layer portion forming a passageway parallel to the main lumen 11, the passageway having an entrance mouth 61 and an exit mouth 69, the exit mouth 69 closer to the proximal end 13 of the stent graft than the entrance mouth 69, the passageway having a closed condition where the underlap and overlap portions 64, 66 are in contact and an open condition where the underlap and overlap portions 64, 66 are spaced apart to form a vent lumen 40, the wall portion broken by a narrow cut or slot 70, the cut or slot 70 having a first edge 72 and a second edge 74. These edges 72, 74 are the same as the edges 72, 74 shown more clearly on the larger drawing of FIG. 2. The cut or slot 70 is openable by relative radial movement of the first edge 72 away from the second edge 74.

Radiopaque markers 27, 29, 31, 33 are provided to assist with location of the low profile side arms 26, 28, 30, 32 by radiographic techniques. Other radiopaque markers may be provided to assist with location of other parts or regions of the stent graft 10.

In a preferred embodiment of the invention shown in FIG. 13 the stent graft may have dimensions as follows:

| | |
|---|---|
| Overall length | 236 mm |
| Length of proximal portion | 48 mm |
| Length of proximal tapered portion | 43 mm |
| Length of reduced diameter portion | 71 mm |
| Length of distal portion | 68 mm |
| Diameter of proximal portion | 34 mm |
| Diameter of distal portion | 24 mm |
| Diameter of portion of reduced diameter | 20 mm |

In a preferred embodiment of the invention, taking the circumference of the stent graft as a clock face with the anterior point a 12 o'clock, the side branches may be placed as follows:

the celiac artery Distance from proximal end 89 mm, 8 mm diameter, length 18 mm, position 1 o'clock the superior mesenteric artery Distance from proximal end 110 mm, 8 mm diameter, length 21 mm, position 12 o'clock the right renal artery Distance from proximal end 128 mm, 6 mm diameter, length 18 mm, position 10:45 o'clock the left renal artery Distance from proximal end 128 mm, 6 mm diameter, length 18 mm, position 2:45 o'clock The vent lumen 40 shown in FIG. 5 can be opened with the aid of a wire 105. This wire can be pre-loaded into the vent lumen 40 within the stent graft 10 so that after (or during) an operation, a valve opening device in the form of a balloon 110 shown in FIG. 5 can be deployed. The balloon 110 can be slid along the wire 105 up into the vent lumen 40 and then inflated to create a separation between the sheet 80 and the wall portion 62. This then allows re-perfusion of an aneurism and perfusion of blood from within the lumen 11 out towards blood vessels such as intercostals 7 as is shown in FIG. 5.

Other valve opening devices (not shown) may be used.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A stent graft comprising:
   a tubular wall of biocompatible graft material having a main lumen extending longitudinally therethrough, a proximal end, a distal end, and a double layer valve between the proximal end and the distal end;
   the double layer valve comprising an inner layer including a part circumferential sheet of biocompatible graft material, an outer layer including a portion of the wall, and a passageway between the inner layer and the outer layer;
   an entrance mouth communicating with the main lumen and the passageway, and an exit mouth communicating with the passageway;
   the inner layer attached to the wall and positioned overlapping the exit mouth;
   the passageway having a closed condition where the inner layer and the outer layer are in contact and an open condition where the inner layer and the outer layer are spaced apart;
   the passageway being parallel to the main lumen when in a closed condition; and
   wherein the stent graft also comprises at least one internal zig zag stent having at least one strut which biases the inner layer radially outward into contact with the outer layer.

2. The stent graft of claim 1 wherein the exit mouth is substantially crescent shaped when the passageway is in the open condition.

3. The stent graft of claim 1 comprising a plurality of external zig zag stents longitudinally spaced apart on an outside surface of the wall of biocompatible graft material and the at least one internal zig zaq stent having at least first, second, and third struts; the second strut extending between the first and third struts.

4. The stent graft of claim 3 wherein the sheet comprises, a first edge, a second edge opposite the first edge, a distal edge and a proximal edge; the first edge sewn to the wall adjacent to the first strut of the at least one internal ziq zaq stent, the second edge sewn to the wall adjacent to the third strut of the at least one internal zig zag stent, and the proximal edge sewn along a line between a pair of adjacent points of the at least one internal zig zaq stent;
   wherein the sheet is biased radially outwards by the second strut.

5. The stent graft of claim 4 wherein the double layer valve comprises a support wire extending between the pair of adjacent points of the strut.

6. The stent graft of claim 5 wherein the support wire is an inverted U-shape when the proximal end is orientated above the distal end.

7. The stent graft of claim 1 provided with a guide wire extending from beyond the distal end through the entrance mouth and through the passageway and out through the exit mouth, the guide wire provided for guiding a valve opening device.

8. The stent graft of claim 1 wherein the exit mouth is a narrow cut or slot on the wall, the cut or slot having a first edge and a second edge, the cut or slot openable by relative radial movement of the first edge away from the second edge.

9. A stent graft comprising:
   a tubular wall of biocompatible graft material having a main lumen extending longitudinally therethrough, a proximal end, a distal end, and a double layer valve between the proximal end and the distal end;
   the double layer valve comprising an inner layer including a part circumferential sheet of biocompatible graft material, an outer layer including a portion of the wall, and a passageway between the inner layer and and the outer layer;
   an entrance mouth communicating with the main lumen and the passageway and an exit mouth communicating with the passageway; the exit mouth closer to the proximal end of the stent graft than the entrance mouth;
   the inner layer attached to the wall and positioned overlapping the exit mouth;
   the passageway having a closed condition where the inner layer and the outer layer are in contact and an open condition where the inner layer and the outer layer are spaced apart;
   the passageway being parallel to the main lumen when in a closed condition;
   wherein the exit mouth is substantially crescent shaped when the passageway is in the open condition; and
   wherein the stent graft also comprises at least one internal zig zag stent having at least one strut which biases the inner layer radially outward into contact with the outer layer.

10. The stent graft of claim 9 provided with a guide wire extending from beyond the distal end through the entrance mouth and through the passageway and out through the exit mouth, the guide wire provided for guiding a valve opening device.

11. the stent graft of claim 9 wherein the at least one strut lies against the inner layer.

\* \* \* \* \*